US009622932B2

(12) United States Patent
Kim et al.

(10) Patent No.: US 9,622,932 B2
(45) Date of Patent: Apr. 18, 2017

(54) GAIT REHABILITATION ROBOT HAVING PASSIVE MECHANISM FOR SHIFTING CENTER OF GRAVITY

(71) Applicants: Seung-Jong Kim, Seoul (KR); Chang Hwan Kim, Seoul (KR); Jun Ho Choi, Seoul (KR); Chan Yul Jung, Bucheon-si (KR); Jong Min Lee, Gunpo-si (KR)

(72) Inventors: Seung-Jong Kim, Seoul (KR); Chang Hwan Kim, Seoul (KR); Jun Ho Choi, Seoul (KR); Chan Yul Jung, Bucheon-si (KR); Jong Min Lee, Gunpo-si (KR)

(73) Assignee: Korea Institute of Science and Technology, Seoul (KR)

( * ) Notice: Subject to any disclaimer, the term of this patent is extended or adjusted under 35 U.S.C. 154(b) by 582 days.

(21) Appl. No.: 14/062,055

(22) Filed: Oct. 24, 2013

(65) Prior Publication Data

US 2014/0343465 A1 Nov. 20, 2014

(30) Foreign Application Priority Data

May 14, 2013 (KR) ........................ 10-2013-0054405

(51) Int. Cl.
*A61F 5/00* (2006.01)
*A61H 1/02* (2006.01)

(52) U.S. Cl.
CPC ........... *A61H 1/024* (2013.01); *A61H 1/0244* (2013.01); *A61H 1/0266* (2013.01);
(Continued)

(58) Field of Classification Search
CPC ........ A61H 1/02; A61H 1/0237; A61H 1/024; A61H 1/0244; A61H 1/0248;
(Continued)

(56) References Cited

U.S. PATENT DOCUMENTS

| | | | | |
|---|---|---|---|---|
| 5,020,790 | A * | 6/1991 | Beard | A61F 5/0102 482/4 |
| 5,741,222 | A * | 4/1998 | Fiore | A61F 5/0111 602/23 |
| 7,278,954 | B2 | 10/2007 | Kawai et al. | |
| 8,313,448 | B2 | 11/2012 | Shimada et al. | |
| 2015/0173929 | A1* | 6/2015 | Kazerooni | A61F 5/0125 602/16 |

(Continued)

FOREIGN PATENT DOCUMENTS

| | | | |
|---|---|---|---|
| JP | 4503311 | B2 | 4/2010 |
| JP | 2011-525117 | A | 9/2011 |

(Continued)

*Primary Examiner* — Steven Douglas
(74) *Attorney, Agent, or Firm* — NSIP Law

(57) ABSTRACT

The gait rehabilitation robot having a passive mechanism includes: a first auxiliary link member connected to a portion between the pelvis and the knee of a rehabilitating person; a joint coupled to a lower end of the first auxiliary link member; a second auxiliary link member coupled to the lower end of the joint and connected to a portion between the pelvis and the knee of the rehabilitating person; a first spring coupled to an upper end of the first auxiliary link member to prevent introversion and extroversion of a hip point from occurring when the rehabilitating person is walking; a foot support which comes into contact with the foot of the rehabilitating person; an ankle joint for connecting the foot support and the second auxiliary link member; and a second spring coupled to a side of the foot support to compensate an entropion angle.

3 Claims, 8 Drawing Sheets

(52) U.S. Cl.
CPC .................. *A61H 2201/163* (2013.01); *A61H 2201/1635* (2013.01); *A61H 2201/1642* (2013.01)

(58) Field of Classification Search
CPC ...... A61H 1/0251; A61H 1/0262; A61H 3/00; A61H 2003/001; A61H 2003/005; A61H 2201/00; A61H 2201/0173; A61H 2201/018; A61H 2201/1628; A61H 2201/163; A61H 2201/164; A61H 2201/1642; A61H 2203/00; A61H 2203/04; A61H 2203/0406; A61H 2205/00; A61H 2205/088; A61H 2205/10; A61H 2205/102; A61H 2205/106; A61H 2205/108
USPC .................. 601/5, 24, 33, 34, 35; 602/5, 16
See application file for complete search history.

(56) References Cited

U.S. PATENT DOCUMENTS

| | | | | |
|---|---|---|---|---|
| 2015/0272810 | A1* | 10/2015 | Teng ...................... | A61H 1/024 601/34 |
| 2015/0351995 | A1* | 12/2015 | Zoss ...................... | A61H 1/024 623/32 |
| 2016/0113831 | A1* | 4/2016 | Hollander ................ | A61H 3/00 623/31 |

FOREIGN PATENT DOCUMENTS

| | | | |
|---|---|---|---|
| JP | 5075759 | B2 | 8/2012 |
| KR | 10-2010-0044360 | A | 4/2010 |
| KR | 10-2010-0106527 | A | 10/2010 |
| KR | 10-2013-0018422 | A | 2/2013 |
| WO | WO 2009/082249 | A2 | 12/2008 |
| WO | WO 2009/082249 | A2 | 7/2009 |

* cited by examiner

GAIT REHABILITATION ROBOT HAVING PASSIVE MECHANISM FOR SHIFTING CENTER OF GRAVITY

CROSS-REFERENCE TO RELATED APPLICATION

This application claims priority to Korean Patent Application No. 10-2013-0054405, filed on May 14, 2013, and all the benefits accruing therefrom under 35 U.S.C. §119, the contents of which in its entirety are herein incorporated by reference.

BACKGROUND

1. Field

The present disclosure relates to a gait rehabilitation robot having a passive mechanism, and more particularly, to a gait rehabilitation robot having a component capable of relieving a force generated at a joint portion which prevent user's ankles from going through an excessive force.

2. Description of the Related Art

A gait rehabilitation robot is a device for assisting a patient, having a lower half paralysis or deterioration because of aging or muscle weakening, to perform gait training without giving an excessive force to the leg. The gait rehabilitation robot is classified into a type which is directly worn by a patient in any time from gait training to daily life and, also, into a type which can be installed at a treadmill so that a patient may repeatedly perform gait training.

FIGS. 1*a* and 1*b* are diagrams showing the change of angle occurring at the lower extremity when a pedestrian stops on the ground and is walking.

Referring to FIG. 1*a*, in the case a pedestrian stops on the ground, based on the pelvis, the lower extremity including the hip joint and the ankle joint is perpendicular to the ground.

Meanwhile, referring to FIG. 1*b*, in the case (of) a pedestrian is walking, the center of gravity shifts according to the movement of the pelvis, and at the lower extremity supported by the ground, particularly the hip joint and the ankle joint, angles $\alpha$, $\beta$ change due to extroversion/introversion and eversion/entropion.

If the change of angle occurs at the lower extremity as shown in FIG. 1*b* during the user's performance, a mechanism for compensating such change of angle should be implemented. If such a mechanism is not implemented, as shown in the enlarged portion of FIG. 1*b*, a rigid body in contact with the foot of the rehabilitating person is separated from the ground or the treadmill, and an excessive force is applied to the ankle joint and the hip joint. In other case, the foot of the rehabilitating person may be pulled along the shifting direction of the center of gravity.

In this regard, Korean Unexamined Patent Publication No. 2010-0044360 discloses a wheelchair-type gait assisting robot, in which the arm and the exoskeleton are integrally coupled without any need of separating, and an ankle driving device is located at the exoskeleton, instead of the arm, to prevent problems caused when the arm and the exoskeleton are separated. In addition, Korean Unexamined Patent Publication No. 2010-0106527 discloses a gait assisting device, which includes an exoskeleton, a power source configured as a battery pack or another similar embedded power pack, a power cable coupled thereto, and a control system.

In case of a general gait rehabilitation robot, a mechanism for compensating the change of angle of the lower extremity is absent or the lower extremity is vertically fixed on the ground, which disturbs natural gait training. In other words, since a general gait rehabilitation robot does not have a component for relieving a force caused by introversion and extroversion at an ankle portion, when a rehabilitating person performs rehabilitation training, an excessive force is applied to the ankle of the rehabilitating person.

Therefore, there is a demand for the development of a device capable of ensuring a user to stably perform gait training without applying an excessive force to an ankle of a rehabilitating person wearing the gait rehabilitation robot and performing gait training.

RELATED LITERATURES

Patent Literature

Korean Unexamined Patent Publication No. 2010-0044360 (Sogang Industry University Cooperation Foundation) Apr. 30, 2010

Korean Unexamined Patent Publication No. 2010-0106527 (Rex Bionics Ltd.) Oct. 1, 2010

SUMMARY

The present disclosure is directed to providing a gait rehabilitation robot having a passive mechanism, which may compensate introversion/extroversion of a hip joint and an entropion angle/eversion angle of an ankle, occurring when a rehabilitating person is walking.

In one aspect, it provides a gait rehabilitation robot having a passive mechanism includes: a first auxiliary link member connected to a portion between the pelvis and the knee of a rehabilitating person; a joint coupled to a lower end of the first auxiliary link member; the second auxiliary link member coupled to the lower end of the joint and connected to a portion between the pelvis and the knee of the rehabilitating person; the first spring coupled to an upper end of the first auxiliary link member to prevent introversion and extroversion of a hip point from occurring when the rehabilitating person is walking; a foot support which comes into contact with the foot of the rehabilitating person; an ankle joint for connecting the foot support and the second auxiliary link member; and the second spring coupled to a side of the foot support to compensate an entropion angle and an eversion angle of the ankle which occurs when the rehabilitating person is walking.

The first spring or the second spring may be a leaf spring.

One end of the first spring may be fixed to a first fixing member, the other end of the first spring may be coupled to the first rotating member, and an elastic deformation may occur according to a pivotal movement of the first rotating member.

One end of the second spring may be fixed to the second fixing member, the other end of the second spring may be coupled to the second rotating member, and an elastic deformation may occur according to a pivotal movement of the second rotating member.

An upper contact member for supporting a portion between the pelvis and the knee of the rehabilitating person may be coupled to an inner end of the first auxiliary link member.

A lower contact member for supporting a portion between the knee and the ankle of the rehabilitating person may be coupled to an inner end of the second auxiliary link member.

Since the gait rehabilitation robot with a passive mechanism may compensate introversion/extroversion of a hip joint and an entropion angle/eversion angle of an ankle, which occurs when a rehabilitating person is walking, it is possible to prevent an excessive force from being applied to the ankle of the rehabilitating person.

In addition, since the gait rehabilitation robot with a passive mechanism according to the present disclosure reproduces a normal heel strike situation when the foot of a rehabilitating person initially comes into contact with the ground, a normal pressure distribution may be formed when the rehabilitating person is walking.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION

Hereinafter, a gait rehabilitation robot according to an embodiment of the present disclosure will be described in detail with reference to the accompanying drawings.

Figure 1A:
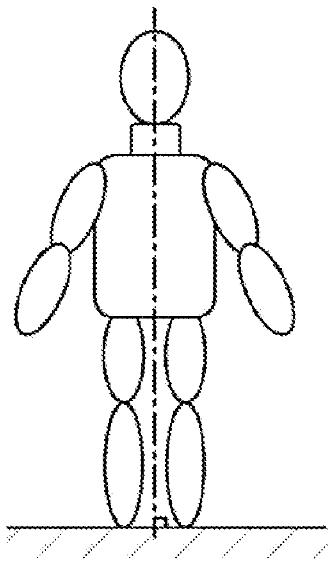
FIGS. 1*a* and 1*b* are diagrams showing the change of angle occurring at the lower extremity when a pedestrian stops on the ground and is walking.
Figure 1B:
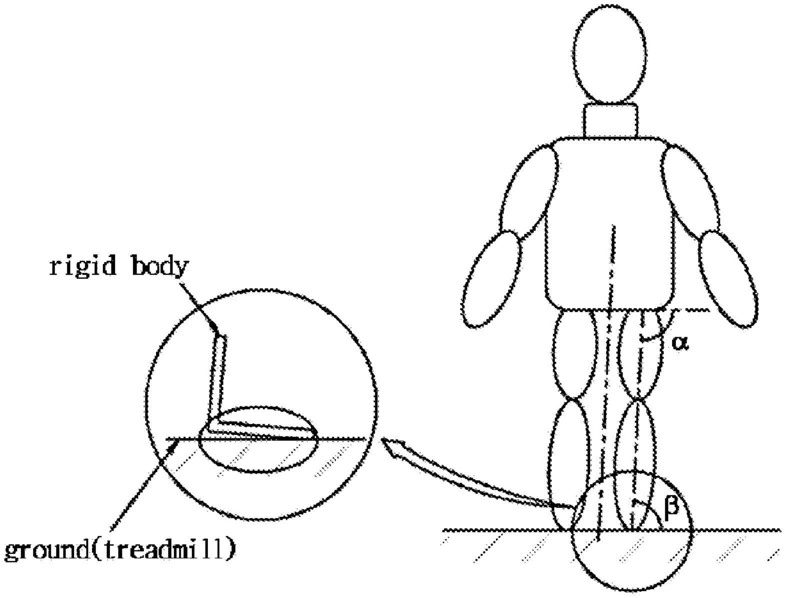
Figure 2:
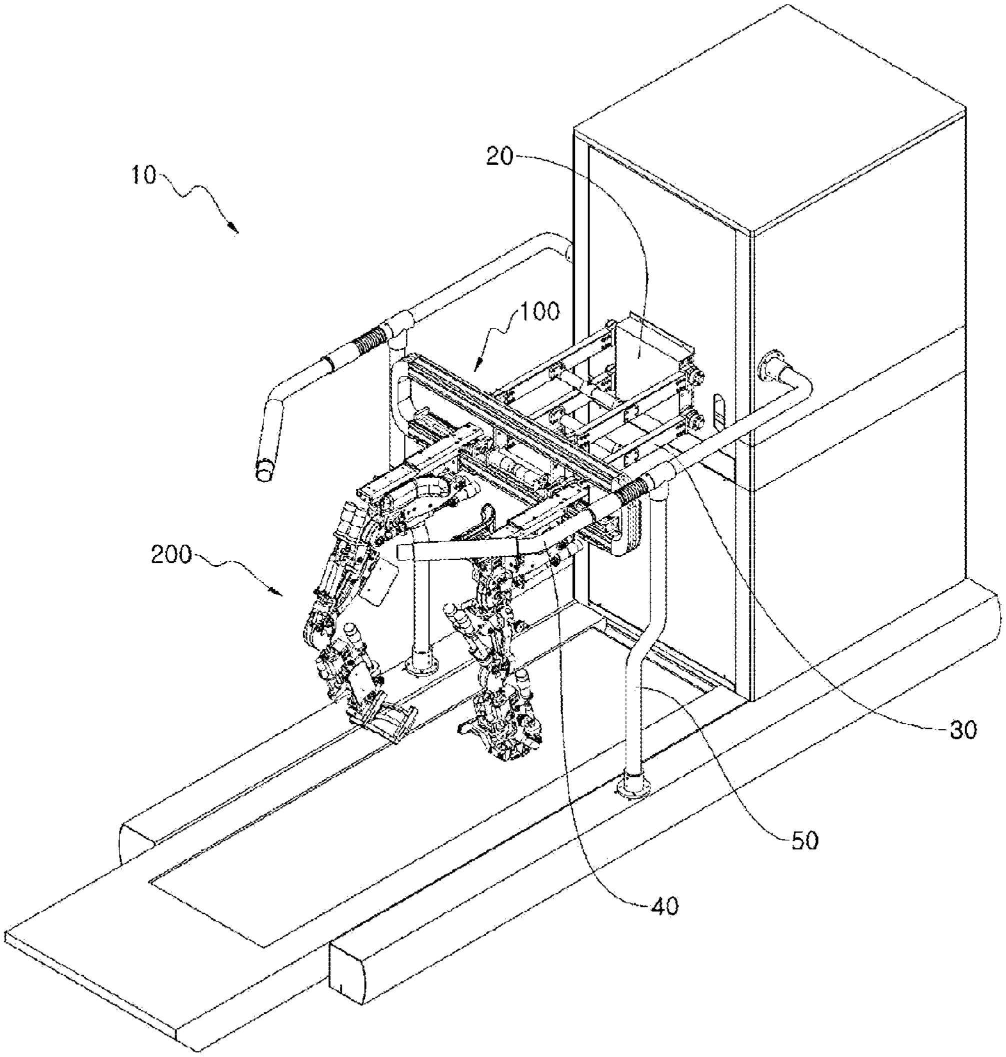
FIG. 2 is a schematic view showing a gait rehabilitation robot having a passive mechanism according to an embodiment of the present disclosure.

FIG. 2 is a schematic view showing a gait rehabilitation robot having a passive mechanism according to an embodiment of the present disclosure.

Referring to FIG. 2, a gait rehabilitation robot 10 includes a fixing frame 20, a connection link 30, a handle 40, a support rod 50, a pelvis support device 100 and a gait assisting link member 200.

The connection link 30 extends from one side of the fixing frame 20 and transfers loads of the gait assisting link member 200 and the pelvis support device 100 toward the fixing frame 20.

The handle 40 is gripped by the hand for safe gait when a rehabilitating person performs rehabilitation training using the gait rehabilitation robot 10. The support rod 50 fixes the handle 40 and is coupled to a part of the handle 40 in order to burden the load of the rehabilitating person.

The pelvis support device 100 supports the pelvis of the rehabilitating person and serves as an assisting unit for a natural gait pattern.

The gait assisting link member 200 is connected to the leg of the rehabilitating person. The rehabilitating person may perform rehabilitation training such as muscle strengthening by connecting the gait assisting link member 200 to the leg and performing leg exercise according to the movement of the gait assisting link member 200.

Figure 3:
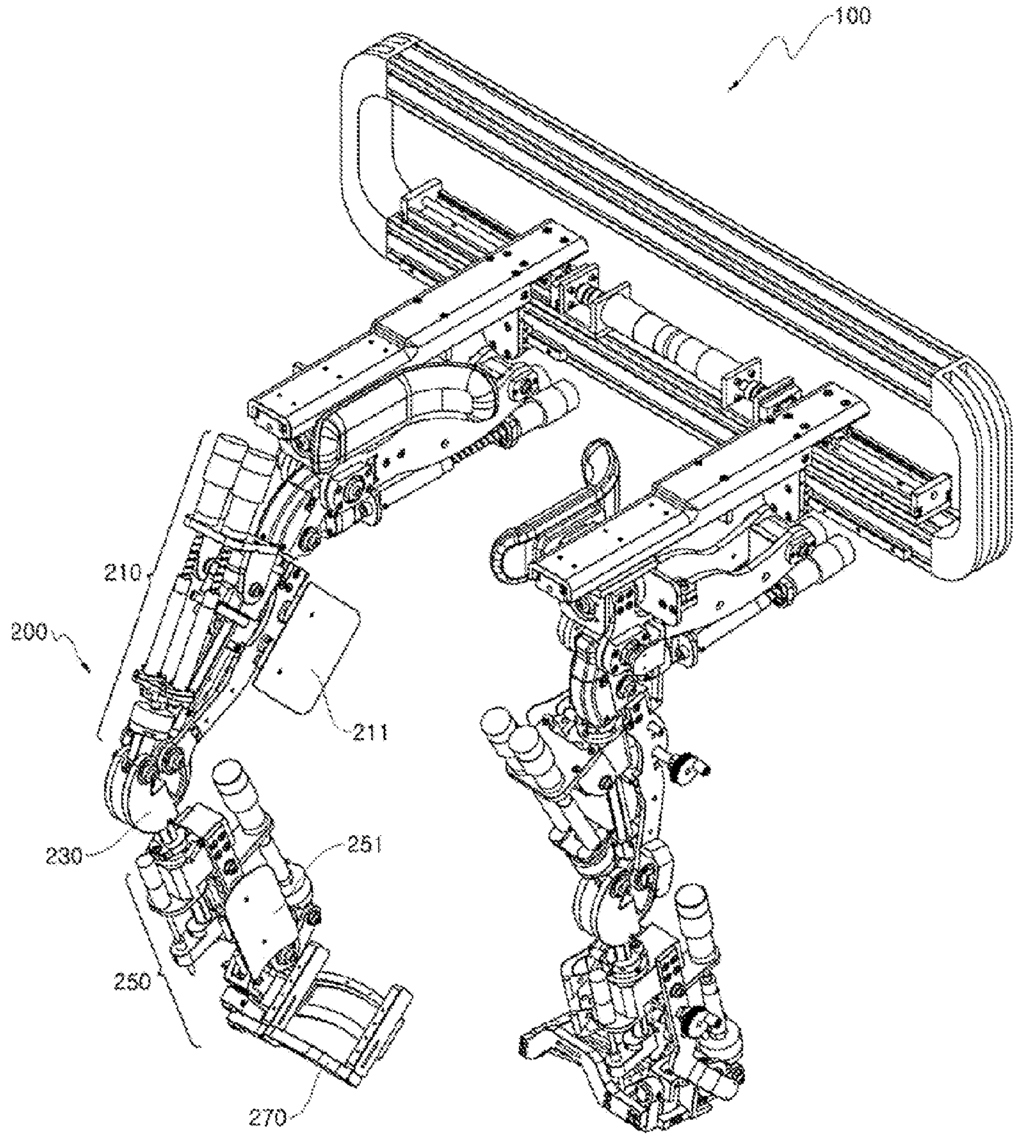
FIG. 3 is a perspective view showing the gait rehabilitation robot according to an embodiment of the present disclosure.

FIG. 3 is a perspective view showing the gait rehabilitation robot according to an embodiment of the present disclosure.

Referring to FIG. 3, the gait rehabilitation robot 10 includes a pelvis support device 100 and a gait assisting link member 200.

The pelvis support device 100 is connected to the gait assisting link member 200 and supports the load of the gait assisting link member 200.

The gait assisting link member 200 includes a first auxiliary link member 210, a joint 230, a second auxiliary link member 250 and a foot support 270.

The first auxiliary link member 210 is connected to a portion between the pelvis and the knee of the rehabilitating person and configured as an assembly in which a plurality of links are coupled to maintain mechanical rigidity and to conform to the leg shape of a user. An upper contact member 211 for supporting the portion between the pelvis and the knee of the rehabilitating person may be coupled to an inner end of the first auxiliary link member 210.

The joint 230 connects the first auxiliary link member 210 and the second auxiliary link member 250, and the first auxiliary link member 210 and the second auxiliary link member 250 may pivot within a predetermined angle based on the joint 230.

The second auxiliary link member 250 is coupled to the lower end of the joint 230 and connected to a portion between the knee and the ankle of the rehabilitating person. The second auxiliary link member 250 is also an assembly in which a plurality of links are coupled to maintain mechanical rigidity and to conform to the leg shape of a user. A lower contact member 251 for supporting the portion between the knee and the ankle of the rehabilitating person may be coupled to an inner end of the second auxiliary link member 250.

The foot support 270 allows the foot of the rehabilitating person to come into contact.

Hereinafter, a gait rehabilitation robot of the present disclosure capable of compensating introversion/extroversion of the hip joint and an entropion angle/eversion angle of the ankle, occurring when a rehabilitating person is walking, by using a spring will be described.

Figure 4:
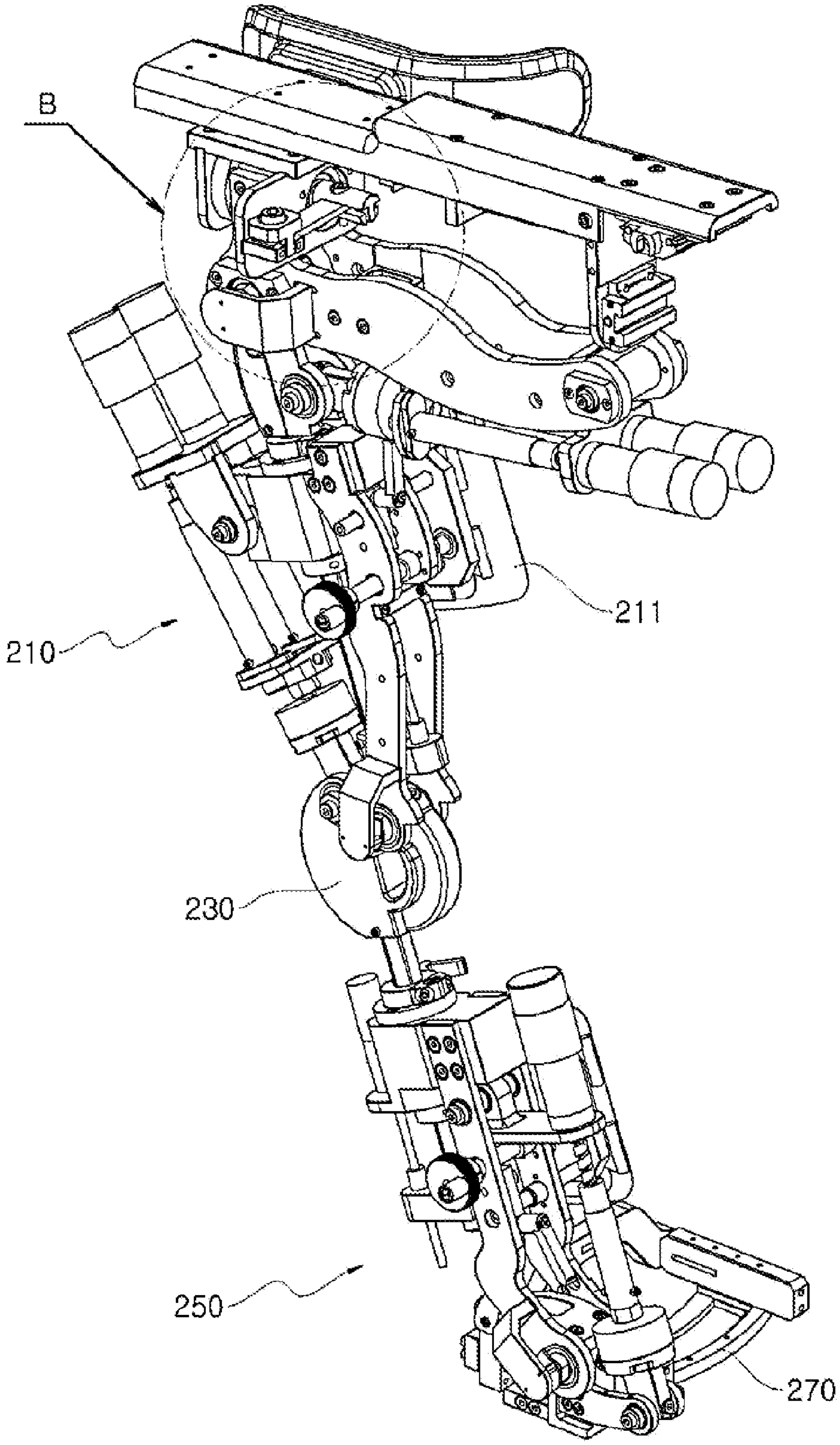
FIG. 4 is a perspective view showing a gait assisting link member of FIG. 3 at one side, observed from the back.
Figure 5:
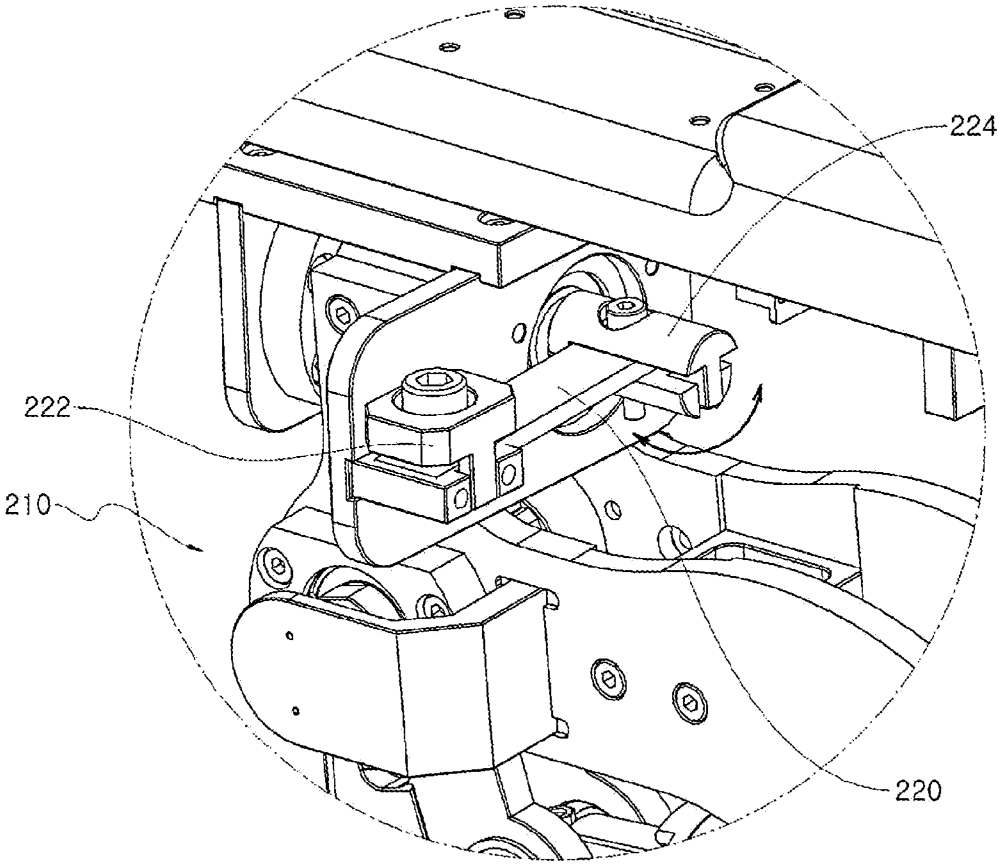
FIG. 5 is an enlarged view showing the portion B of FIG. 4.

FIG. 4 is a perspective view showing the gait assisting link member of FIG. 3 at one side, observed from the back, and FIG. 5 is an enlarged view showing the portion B of FIG. 4.

Referring to FIGS. 4 and 5, the first spring 220 is coupled to an upper end of the first auxiliary link member 210 and prevents introversion and extroversion of the hip joint when the rehabilitating person is walking. The first spring 220 may be, for example, a leaf spring. One end of the first spring 220 is fixed to the first fixing member 222, the other end of the first spring 220 is coupled to the first rotating member 224, and an elastic deformation is generated according to a pivotal movement of the first rotating member 224.

Figure 6A:
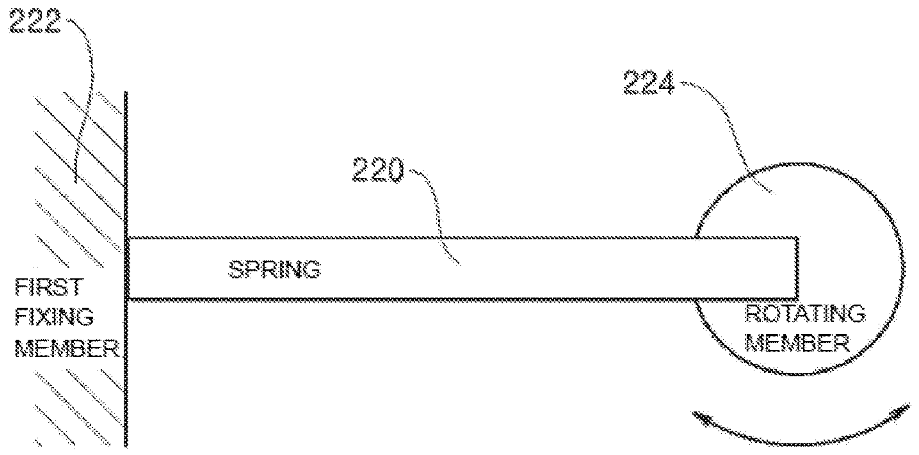
FIGS. 6*a* and 6*b* are diagrams for illustrating an operating principle of the passive mechanism.
Figure 6B:
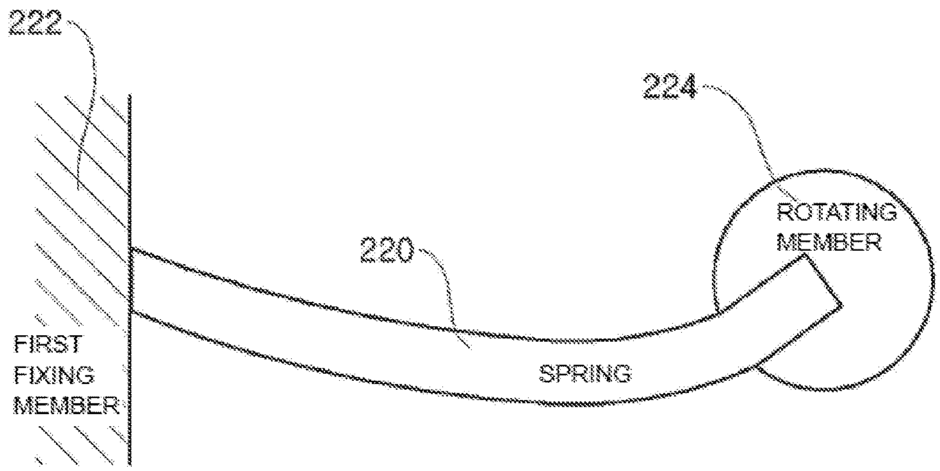

FIGS. 6*a* and 6*b* are diagrams for illustrating an operating principle of the passive mechanism.

Referring to FIGS. 6*a* and 6*b*, the first spring 220, the first fixing member 222 and the first rotating member 224 of FIG. 4 are depicted in brief. One end of the first spring 220 coupled to the first fixing member 222 is fixed, and the other end of the first spring 220 is coupled to the first rotating member 224. The first rotating member 224 is connected to the first auxiliary link member 210, and when the rehabilitating person is walking, if the first auxiliary link member 210 pivots right or left according to the movement of the pelvis, the first rotating member 224 connected thereto also pivots right and left. Accordingly, the first spring 220 is curved and generates an elastic force, which prevents introversion and extroversion of the hip joint which occurs when the rehabilitating person is walking. FIG. 6*b* shows an elastic deformation of the first spring 220 when the first rotating member 224 rotates in a counterclockwise direction.

Figure 7:
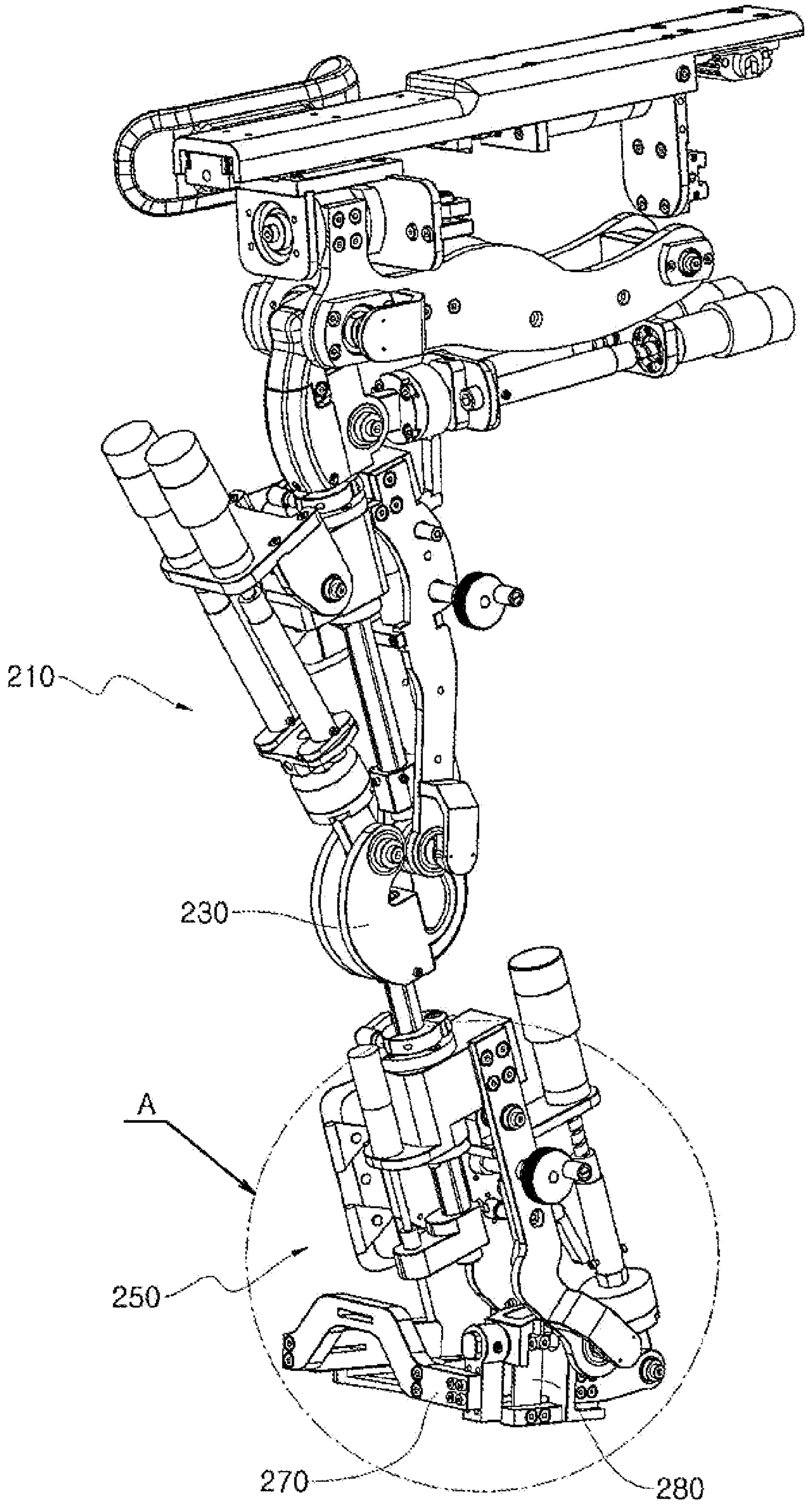
FIG. 7 is a perspective view showing the gait assisting link member of FIG. 3 at one side.
Figure 8:
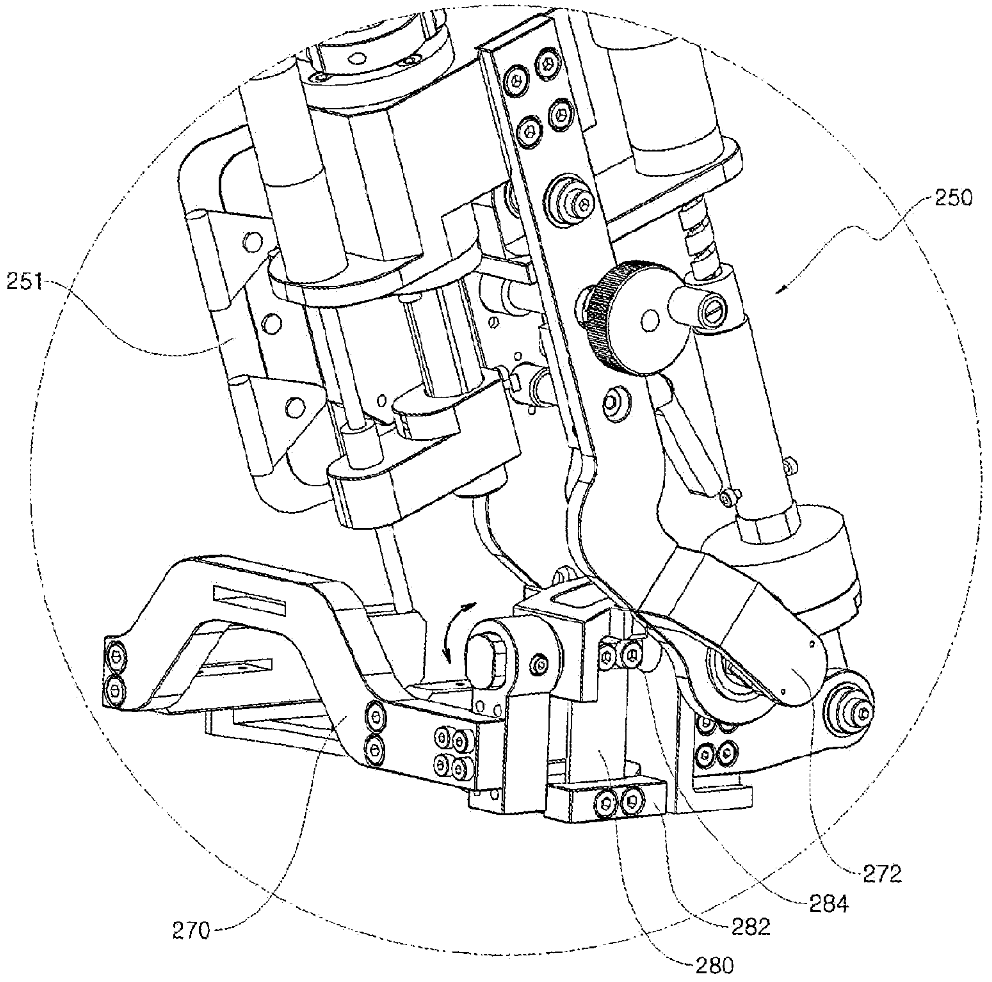
FIG. 8 is an enlarged view showing the portion A of FIG. 7.

FIG. 7 is a perspective view showing the gait assisting link member of FIG. 3 at one side, and FIG. 8 is an enlarged view showing the portion A of FIG. 7.

Referring to FIGS. 7 and 8, the foot support 270 coming into contact with the foot of the rehabilitating person is connected to the second auxiliary link member 250 by means of the ankle joint 272.

The second spring 280 is coupled to a side of the foot support 270, and compensates an entropion angle and eversion angle of the ankle which occurs when the rehabilitating person is walking. The second spring 280 is, for example, a leaf spring.

In one embodiment of the present disclosure, one end of the second spring 280 is fixed to the second fixing member 282, the other end of the second spring 280 is coupled to the second rotating member 284, and an elastic deformation is generated according to a pivotal movement of the second rotating member 284. Here, the second rotating member 284 is coupled to the foot support 270, and if the foot support 270 pivots upwards or downwards, the second rotating member 284 also pivots upwards or downwards. Accordingly, the second spring 280 is curved and generates an elastic force, which may compensate an entropion angle and eversion angle of the ankle which occurs when the rehabilitating person is walking.

While the exemplary embodiments have been shown and described, it will be understood by those skilled in the art that the present disclosure is not limited thereto but various changes in form and details may be made thereto without departing from the spirit and scope of the present disclosure as defined by the appended claims.

What is claimed is:

1. A gait rehabilitation robot, comprising:

a first auxiliary link member configured to be connected to a portion between a pelvis and a knee of a subject;

a joint coupled to a lower end of the first auxiliary link member;

a second auxiliary link member coupled to a lower end of the joint and configured to connect to a portion between the knee and a foot of the subject;

a first spring coupled to an upper end of the first auxiliary link member;

a foot support configured to contact the foot of the subject;

an ankle joint connecting the foot support and the second auxiliary link member; and a second spring coupled to a side of the foot support, wherein a first end of the first spring is fixed to a first fixing member, a second end of the first spring is coupled to a first rotating member, and an elastic deformation occurs according to a pivotal movement of the first rotating member, and wherein a first end of the second spring is fixed to a second fixing member, a second end of the second spring is coupled to a second rotating member, and an elastic deformation occurs according to a pivotal movement of the second rotating member.

2. The gait rehabilitation robot according to claim 1, wherein the first spring is a leaf spring.

3. The gait rehabilitation robot according to claim 1, wherein the second spring is a leaf spring.

* * * * *